(12) United States Patent
Youngbull et al.

(10) Patent No.: US 11,618,030 B2
(45) Date of Patent: Apr. 4, 2023

(54) SYSTEMS AND METHODS FOR CONTINUOUS FLOW DIGITAL DROPLET POLYMERASE CHAIN REACTION BIOANALYSIS

(71) Applicant: Arizona Board of Regents on Behalf of Arizona State University, Scottsdale, AZ (US)

(72) Inventors: Cody Youngbull, Tempe, AZ (US); Andrew Hatch, Tempe, AZ (US); Tathagata Ray, Tempe, WA (US); Andrew Larsen, Scottsdale, AZ (US); Matthew Underhill, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/389,253

(22) Filed: Jul. 29, 2021

(65) Prior Publication Data
US 2022/0193681 A1    Jun. 23, 2022

Related U.S. Application Data

(63) Continuation of application No. 15/739,318, filed as application No. PCT/US2016/040172 on Jun. 29, 2016, now Pat. No. 11,123,740.
(Continued)

(51) Int. Cl.
*B01L 7/00*   (2006.01)
*G01N 35/10*  (2006.01)
(Continued)

(52) U.S. Cl.
CPC ............. *B01L 7/52* (2013.01); *B01L 3/50851* (2013.01); *C12Q 1/686* (2013.01); *G01N 1/10* (2013.01);
(Continued)

(58) Field of Classification Search
CPC . B01L 2200/0673; B01L 7/52; B01F 13/0071
See application file for complete search history.

(56) References Cited

U.S. PATENT DOCUMENTS 6,143,496 A    11/2000  Brown et al.
6,767,706 B2   7/2004   Quake et al.
(Continued)

FOREIGN PATENT DOCUMENTS

CN    104114282 A    10/2014
EP    1574586 B1     11/2012
(Continued)

OTHER PUBLICATIONS

Han et al.: An active microfluidic system packaging technology. Sensors and Actuators B Chemical 122(1):337-346 doi:10.1016/j.snb.2006.06.028 (2007).
(Continued)

*Primary Examiner* — Jonathan M Hurst
(74) *Attorney, Agent, or Firm* — Wilson Sonsini Goodrich & Rosati

(57) ABSTRACT

Systems and methods for continuous flow polymerase chain reaction (PCR) are provided. The system comprises an injector, a mixer, a coalescer, a droplet generator, a detector, a digital PCR system, and a controller. The injector takes in a sample, partitions the sample into sample aliquots with the help of an immiscible oil phase, dispenses waste, and sends the sample aliquot to the mixer. The mixer mixes the sample aliquot with a PCR master mix and diluting water, dispenses waste, and sends the sample mixture (separated by an immiscible oil) to the coalescer. The coalescer coalesces the sample mixture with primers dispensed from a cassette, dispenses waste, and sends the reaction mixture (separated by an immiscible oil) to the droplet generator. The droplet generator converts the sample mixture into an emulsion where aqueous droplets of the reaction mixture are main-
(Continued)

tained inside of an immiscible oil phase and dispenses droplets to the digital PCR system. The digital PCR system amplifies target DNAs in the droplets. The detector detects target DNAs in the droplets. The controller controls the system to run automatically and continuously.

19 Claims, 11 Drawing Sheets

Related U.S. Application Data

(60) Provisional application No. 62/186,321, filed on Jun. 29, 2015.

(51) Int. Cl.
   *B01L 3/00* (2006.01)
   *C12Q 1/686* (2018.01)
   *G01N 1/10* (2006.01)
   *G01N 35/00* (2006.01)
   *B01F 33/302* (2022.01)

(52) U.S. Cl.
   CPC ...... *G01N 35/1095* (2013.01); *B01F 33/3021* (2022.01); *B01L 2200/0673* (2013.01); *G01N 2035/00465* (2013.01); *G01N 2035/1032* (2013.01); *G01N 2035/1034* (2013.01)

(56) References Cited

U.S. PATENT DOCUMENTS

| | | |
|---|---|---|
| 6,960,437 B2 | 11/2005 | Enzelberger et al. |
| 6,977,145 B2 | 12/2005 | Fouillet et al. |
| 7,129,091 B2 | 10/2006 | Ismagilov et al. |
| 7,268,167 B2 | 9/2007 | Higuchi et al. |
| 7,294,503 B2 | 11/2007 | Quake et al. |
| 7,622,081 B2 | 11/2009 | Chou et al. |
| 7,772,287 B2 | 8/2010 | Higuchi et al. |
| RE41,780 E | 9/2010 | Anderson et al. |
| RE43,365 E | 5/2012 | Anderson et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,399,198 B2 | 3/2013 | Hiddessen et al. |
| 8,633,015 B2 | 1/2014 | Ness et al. |
| 8,709,762 B2 | 4/2014 | Hindson |
| 8,730,479 B2 | 5/2014 | Ness et al. |
| 8,771,747 B2 | 7/2014 | O'Hagan et al. |
| 8,822,148 B2 | 9/2014 | Ismagliov et al. |
| 8,841,093 B2 | 9/2014 | Takahashi et al. |
| 8,871,444 B2 | 10/2014 | Griffiths et al. |
| 8,889,083 B2 | 11/2014 | Ismagilov et al. |
| 8,951,732 B2 | 2/2015 | Pollack et al. |
| 9,012,390 B2 | 4/2015 | Holtze et al. |
| 9,029,083 B2 | 5/2015 | Griffiths et al. |
| 9,056,289 B2 | 6/2015 | Weitz et al. |
| 9,074,242 B2 | 7/2015 | Larson et al. |
| 9,127,310 B2 | 9/2015 | Larson et al. |
| 9,132,394 B2 | 9/2015 | Makarewicz, Jr. et al. |
| 9,156,010 B2 | 10/2015 | Colston et al. |
| 9,181,375 B2 | 11/2015 | Tian et al. |
| 9,216,392 B2 | 12/2015 | Hindson et al. |
| 9,222,115 B2 | 12/2015 | Marble et al. |
| 9,243,288 B2 | 1/2016 | Ness et al. |
| 9,248,417 B2 | 2/2016 | Hindson et al. |
| 9,273,308 B2 | 3/2016 | Link et al. |
| 9,366,632 B2 | 6/2016 | Link et al. |
| 9,441,266 B2 | 9/2016 | Larson et al. |
| 9,492,797 B2 | 11/2016 | Makarewicz et al. |
| 9,498,761 B2 | 11/2016 | Holtze et al. |
| RE46,322 E | 2/2017 | Anderson et al. |
| 9,562,837 B2 | 2/2017 | Link |
| 9,597,026 B2 | 3/2017 | Meldrum et al. |
| 9,752,141 B2 | 9/2017 | Link et al. |
| 9,968,933 B2 | 5/2018 | Ismagilov et al. |
| 11,123,740 B2 | 9/2021 | Youngbull et al. |
| 11,413,616 B2 | 8/2022 | Youngbull et al. |
| 2005/0227264 A1 | 10/2005 | Nobile et al. |
| 2006/0257893 A1 | 11/2006 | Takahashi et al. |
| 2008/0014589 A1 | 1/2008 | Link et al. |
| 2012/0115738 A1 | 5/2012 | Zhou et al. |
| 2012/0231533 A1 | 9/2012 | Holl et al. |
| 2012/0301913 A1 | 11/2012 | Youngbull et al. |
| 2012/0302448 A1 | 11/2012 | Hutchison et al. |
| 2014/0045712 A1 | 2/2014 | Link et al. |
| 2014/0193800 A1 | 7/2014 | Aguanno et al. |
| 2014/0199730 A1 | 7/2014 | Agresti et al. |
| 2014/0199731 A1 | 7/2014 | Agresti et al. |
| 2014/0202546 A1 | 7/2014 | Ismagilov et al. |
| 2014/0208832 A1 | 7/2014 | Hansen et al. |
| 2015/0018236 A1 | 1/2015 | Green et al. |
| 2016/0177375 A1 | 6/2016 | Abate et al. |
| 2022/0288591 A1 | 9/2022 | Youngbull et al. |

FOREIGN PATENT DOCUMENTS

| | | |
|---|---|---|
| EP | 1735458 B1 | 7/2013 |
| WO | WO-2010022391 A2 | 2/2010 |
| WO | WO-2010036352 A1 | 4/2010 |
| WO | WO-2010062654 A2 | 6/2010 |
| WO | WO-2012112440 A2 | 8/2012 |
| WO | WO-2013165748 A1 | 11/2013 |
| WO | WO-2014008381 A2 | 1/2014 |
| WO | WO-2014210207 A1 | 12/2014 |
| WO | WO-2017004250 A1 | 1/2017 |
| WO | WO-2018098438 A1 | 5/2018 |

OTHER PUBLICATIONS

Moscovici et al.: Electrical power free, low dead volume, pressure-driven pumping for microfluidic applications. Biomicrofluidics. Oct. 13, 2010;4(4):46501:1-10 doi:10.1063/1.3499939 (2010).

Chabert et al.: Droplet fusion by alternating current (AC) field electrocoalescence in microchannels. Electrophoresis 26(19):3706-3715 (2005).

Eow, et al. Electrostatic Enhancement of Coalescence of Water Droplets in Oil: a Review of the Current Understanding. Chemical engineering Journal 84 (3):173-192 (Dec. 15, 2001).

Hatch, Andrew et al. Continuous flow real-time PCR device using multi-channel fluorescence excitation and detection. Lab on a Chip, 14(3):562-568 (Nov. 19, 2013).

International Application No. PCT/US16/40172 International Preliminary Report on Patentability dated Jan. 2, 2018.

International Application No. PCT/US2016/040172 International Search Report and Written Opinion dated Oct. 20, 2016.

International Application No. PCT/US2017/063293 International Search Report and Written Opinion dated Jan. 18, 2018.

Mazutis, et al. Single-Cell Analysis and Sorting Using Droplet-Based Microfluidics. Nat Protoc. 8(5): 870-891 (May 2013).

Tathagata, Ray et al. Low Power, High Throughput Continuous Flow PCR Instruments for Environmental Applications. (Retrieved from the Internet: Jan. 10, 2018) Dec. 1, 2013, pp. 1-181.

U.S. Appl. No. 15/739,318 Final Office Action dated Dec. 4, 2020.
U.S. Appl. No. 16/413,416 Final Office Action dated Jul. 26, 2021.
U.S. Appl. No. 16/413,416 Non-Final Office Action dated Dec. 22, 2020.
U.S. Appl. No. 15/739,318 Non-Final Office Action dated Aug. 27, 2020.

SYSTEMS AND METHODS FOR CONTINUOUS FLOW DIGITAL DROPLET POLYMERASE CHAIN REACTION BIOANALYSIS

CROSS-REFERENCE TO RELATED APPLICATIONS

This patent application is a continuation of U.S. application Ser. No. 15/739,318 filed Dec. 22, 2017, which is a national stage application under 35 USC 371 of International Application No. PCT/US2016/040172 filed Jun. 29, 2016, which claims the benefit of U.S. Prov. Pat. App. Ser. No. 62/186,321, filed Jun. 29, 2015, and incorporated fully herein by reference.

BACKGROUND

The technology of polymerase chain reaction has been a common and often indispensable technique in medical and biological studies and applications. Digital PCR (dPCR) allows quantification of DNA in a sample. dPCR is advantageous for reasons of accuracy (absolute titer quantification), sensitivity (single molecule detection), dynamic range, and robustness against inhibition. A mobile dPCR allows immediate quantification of samples, but the samples typically need to be purified before a dPCR can be conducted. In addition, a vast amount of samples may need to be tested, compared to typical lab settings.

Systems and methods of a portable continuous flow dPCR device that automates the entire analysis on a continuous flow of samples from a fluid are described herein.

SUMMARY

The present disclosure provides systems and methods that perform digital droplet PCR analysis on a continuous fluid stream. The instrument draws in a sample of molecules, such as DNA in aqueous suspension, mixes and dilutes that sample with PCR mastermix, a diluent such as water, and one or more suitable PCR probes without disrupting flow of the fluid stream significantly. The resultant sample liquid is then broken into droplets that stochastically contain the target molecules. The droplets are then thermocycled to amplify their nucleic acid contents by PCR. In the end, the individual droplets are counted to determine the original starting concentration in the sample.

In accordance with one aspect of the disclosure, a system for continuous flow polymerase chain reaction (PCR) is provided. The system comprises an injector, a mixer a droplet generator, a detector, a digital PCR system, and a controller. The injector takes in a sample from a sample inlet and aliquots the sample into a volume necessary for a PCR reaction, dispenses waste, and hands off the sample aliquots separated by an immiscible oil phase to a mixer one aliquot at a time. The mixer takes in the sample aliquot, mixes it with the PCR master mix and diluting water, dispenses waste, and hands off the sample mixture to a coalescer in aliquots separated by an immiscible oil phase. The coalescer takes in the sample mixture, coalesces it with primers that are dispensed from the cassette, dispenses waste, and hands off the reaction mixture separated by an immiscible oil phase to the droplet generator. The droplet generator converts the sample mixture into an emulsion where aqueous droplets of the reaction mixture are maintained inside of an immiscible oil phase. The aqueous reaction droplets are then passed to the digital PCR system to enable amplification of target molecule (e.g., DNA) molecules in the droplets. Post amplification, a detector determines whether or not target molecule (e.g., DNA) amplification occurred for each of the droplets. The controller processes data outputted from the detector and controls the system so that the system runs automatically and continuously.

In another aspect of this disclosure, a method for continuous flow PCR is provided. First a sample of a fluid stream is taken in at a sample inlet and passed through an injector to produce sample aliquots, with each aliquot being separated by an immiscible oil phase. Each sample aliquot is mixed, e.g., using a mixer, with reagents such as PCR master mix, primers, probes, and diluting water to produce a sample mixture. The primers and/or probes may be PCR primers modified with fluorophores that bind to a target molecule, such as DNA. The reagents may come from a cassette or from reagent storage.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
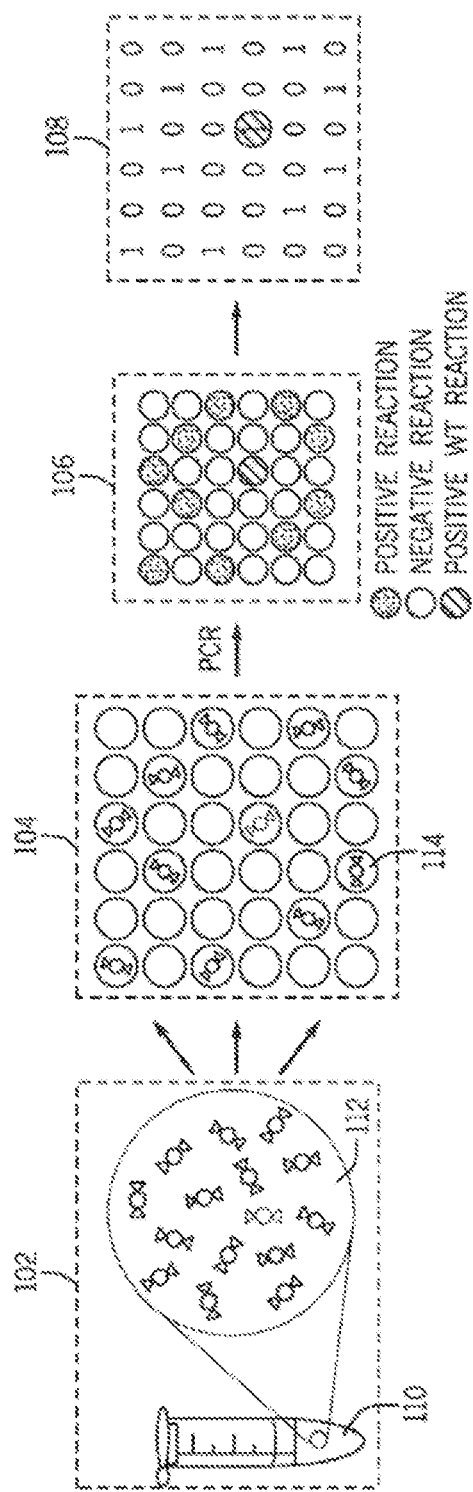
FIG. 1 is a schematic diagram of digital polymerase chain reaction (PCR).

"Polymerase chain reaction" or "PCR" refers to a technology widely used in molecular biology to amplify a single copy or a few copies of DNA across several orders of magnitude, generating thousands to millions of copies of a particular DNA sequence.

The PCR technology uses reaction mixture that comprises DNA templates containing DNA to be amplified, primers, enzyme such as Taq polymerase, deoxynucleoside triphosphates (dNTPs)—the building-blocks from which the DNA polymerase synthesizes a new DNA strand, buffer that provides a suitable chemical environment for the amplifying process, and other chemicals. PCR master mix comprises those components except primers. Primers are short DNA fragments containing sequences complementary to the target region along with a DNA polymerase are used to enable selective and repeated amplification. As PCR progresses, the DNA generated is itself used as a template for replication, setting in motion a chain reaction in which the DNA template is exponentially amplified.

The PCR methods comprises placing the reaction mixture in a thermocycler and, in the thermocycler, undergoing a series of 20-40 repeated temperature changes—called cycles—with each cycle commonly consisting of 2-3 discrete temperature steps. The cycling is often preceded by a single temperature step at a high temperature (>90° C.)—also called hot start, and followed by one hold at the end for final product extension or brief storage. The temperatures used and the length of time in each cycle depend on parameters, such as the enzyme used for DNA synthesis, the concentration of divalent ions and dNTPs in the reaction, and the melting temperature of the primers.

Each cycle usually comprises three steps, melting (or denaturation), annealing, and extension (or elongation). In the melting step, the reaction mixture is heated to 94-98° C. for 20-30 seconds, causing melting of the DNA template to single-stranded DNA molecules by disrupting the hydrogen bonds between complementary bases.

In the annealing step, the reaction temperature is lowered to 50-65° C. for 20-40 seconds allowing annealing—combining—of the primers to the single-stranded DNA template. This temperature is low enough to allow for hybridization of the primer to the strand, but high enough for the hybridization to be specific, i.e., the primer should only bind to a perfectly complementary part of the template. Stable DNA-DNA hydrogen bonds are only formed when the primer sequence very closely matches the template sequence. The polymerase binds to the primer-template hybrid and begins DNA formation.

In the extension step, the DNA polymerase synthesizes a new DNA strand complementary to the DNA template strand by adding dNTPs that are complementary to the template.

Digital PCR follows the same principle and process as those of traditional PCR, except that, in digital PCR, a sample is partitioned into many small partitions such that individual nucleic acid templates of interest can be localized in individual partitions.

Referring to FIG. 1, a schematic illustrating digital PCR is provided. In step 102, bulk sample is placed in tube 110. The bulk sample contains many nucleic acids or DNA, as shown in the insert 112. In step 104, the sample is partitioned into many individual reactors 114. Each of the reactors may or may not contain a target DNA. In step 106, each reactor undergoes a PCR such that the number of target DNAs in a reactor is amplified to a detectable level. In step 108, the partitioned sample is digitally read out, providing quantification.

Figure 2:
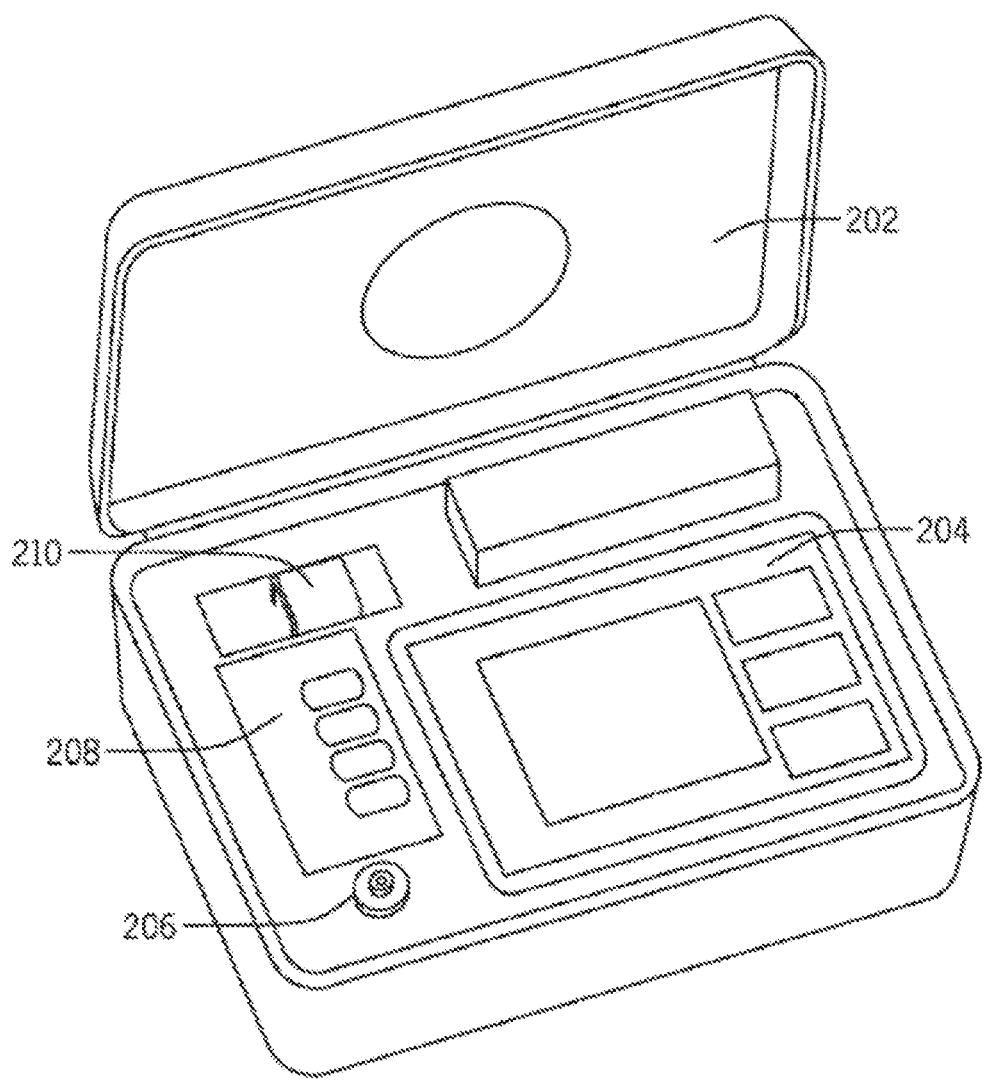
FIG. 2 is a photo of an example system implemented according to the present application.

Referring to FIG. 2, a photo of an example system implemented according to the present application is provided. The system can be enclosed in a brief case 202 equipped with external power outlet. The system provides a sample injection port 206, a reagent bay 208, and a primer library 210. A controller 204 controls the system and analyzes data. The controller can be a tablet PC (as shown in FIG. 2), a laptop, or a mobile device.

Figure 3:
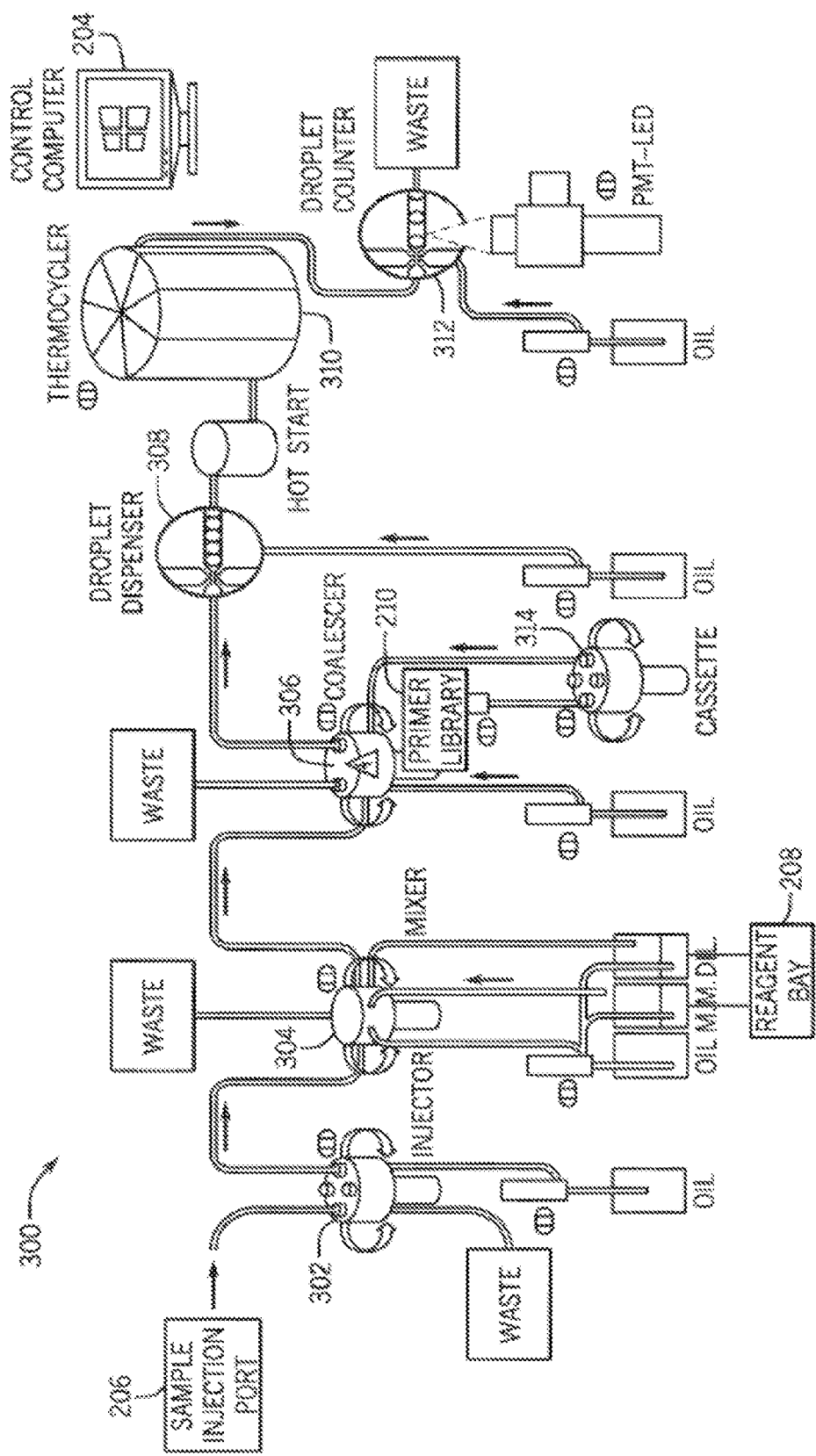
FIG. 3 is a schematic diagram of an example system implemented according to the present application.

Referring to FIG. 3, a schematic illustrating an example system 300 implemented according to the present application is provided. The system comprises an injector 302, a mixer 304, a coalescer 306, a droplet generator 308, a digital PCR system, a detector, and a controller 204. The digital PCR system comprises a thermocyler 310. The detector can comprise a droplet counter 312. The sample injection port 206 provides an inlet for inputting a sample into the injector 302. The reagent bay 208 holds reagents to be mixed with the sample in the mixer 304. The primer library 210 holds primers used to detect the target DNA. The primers from the primer library 210 may be fed to a cassette 314, or the cassette 314 may include the primer library 210. The cassette 314 hands off the primers to the coalescer 306. Then the primers are coalesced with sample mixture in coalescer. The controller 204 controls the system and analyzes the data detected by the detector. As shown in FIG. 3, in the system 300, waste outlets are available at each major step and oil can be used throughout to act as a carrier fluid for the sample. The injector 302, mixer 304, and coalescer 306 can automatically hand off the sample mixture to the next unit so that the sample mixture flows through the system 300 continuously.

Figure 4:
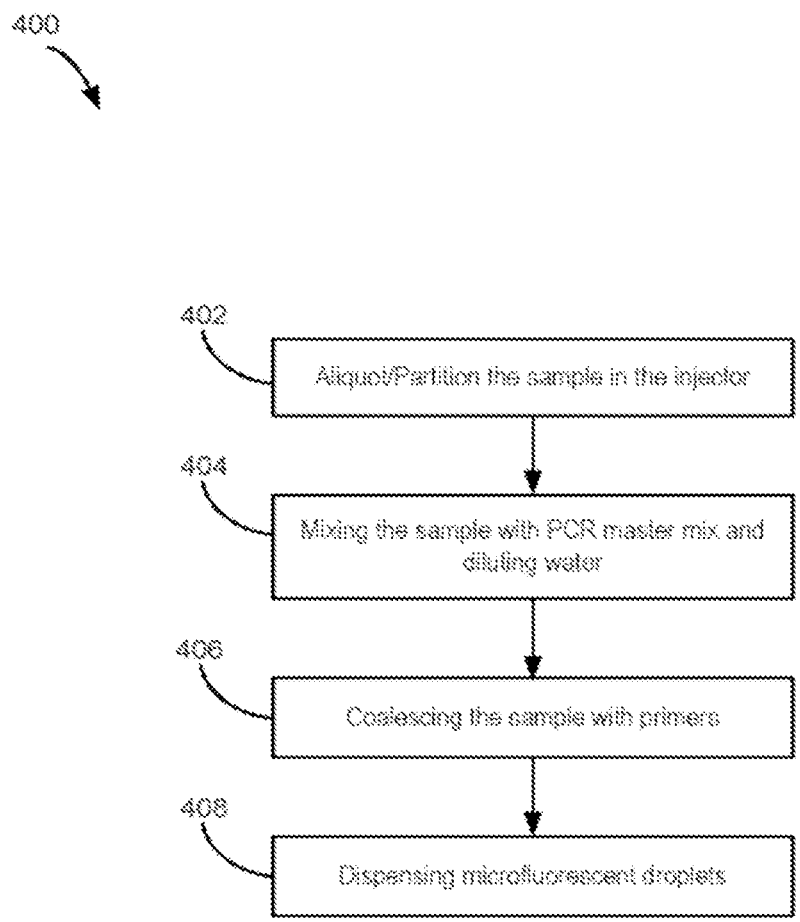
FIG. 4 is an example flowchart illustrating a method implemented according to the present application.

Referring to FIG. 4, a flowchart 400 depicting an example method implemented according to the present application is provided. At step 402, the sample is partitioned with oil in an injector 302. The sample is inputted into the system through a sample injection port 206. Waste is dispensed after the mixing and the ejector 302 hands off the sample mixture to the mixer 304. In step 404, the sample mixture handed off from the injector is mixed in the mixer 304 with the PCR master mix and diluting water. The master mix is held in reagent bay 208. Again, waste is dispensed and the mixer 304 hands the sample mixture off to the coalescer 306. In step 406, the sample mixture is coalesced with primers into reaction mixtures. Fluorescent-labeled primers can be used to detect target DNAs. Also, waste is dispensed. In step 408, the reaction mixture is broken up into droplets using the droplet generator oil and the droplets are dispensed by the droplet generator 308. The droplets can be used in a droplet digital PCR system. For example, the target DNA is amplified with the temperatures cycled and controlled by thermocycler 310. Before the temperature cycles, droplets may go through a hot start step. After the target DNA in the droplets are amplified, the concentration of target DNA in the sample can be detected by counting fluorescent-labeled droplets detectable by photo-multiplier tube LEDs in the mixture of the droplets and oil. Waste is dispensed.

Figure 5:
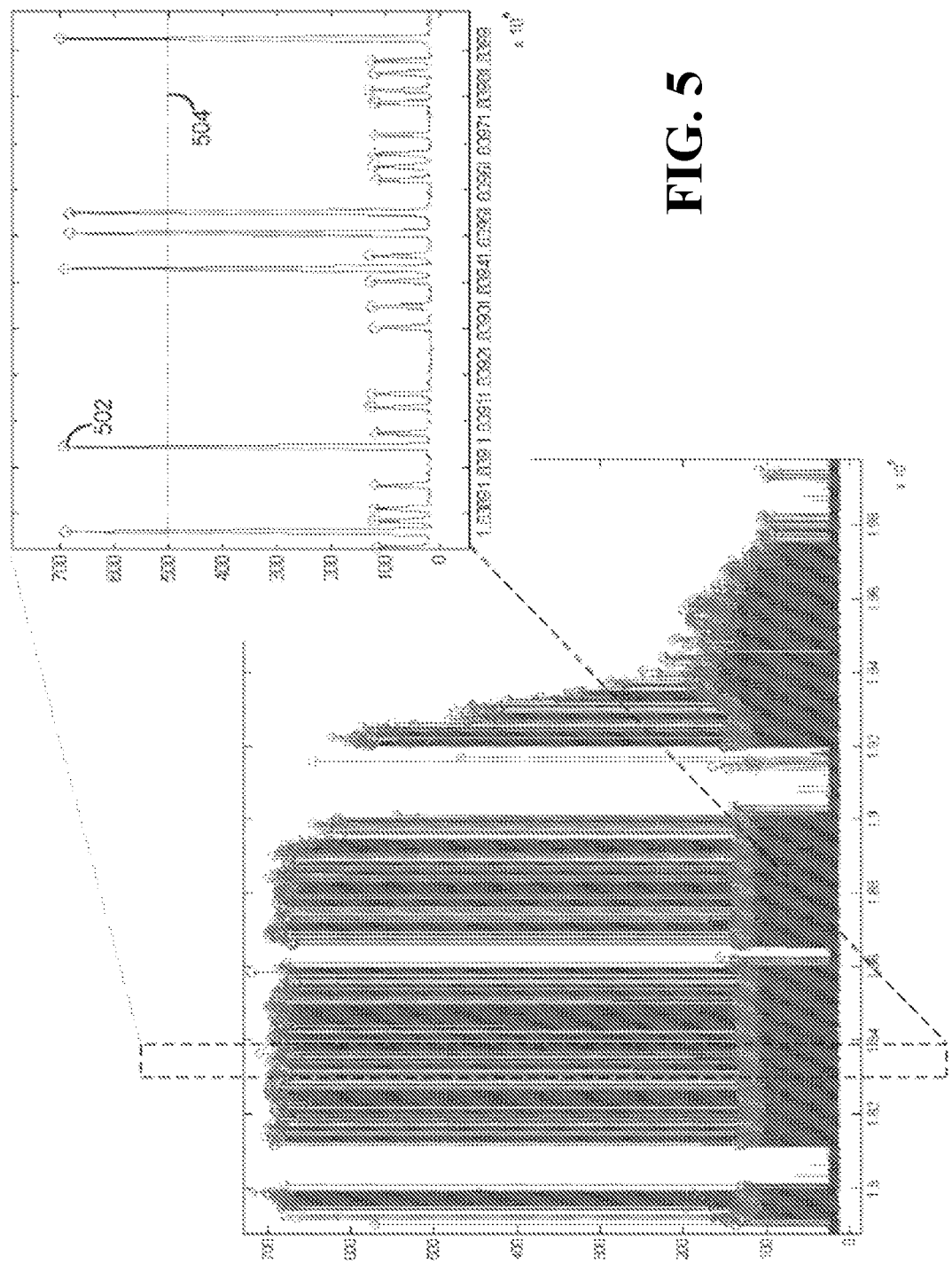
FIG. 5 is an example output from the photomultiplier tube LEDs.

Referring to FIG. 5, an example output from the PMT-LEDs is provided. Each peak marked with a circle denotes the signal of a droplet detected by the PMT-LEDs. When a droplet has target DNA, the target DNA in the droplet is fluorescent labeled due to the fluorescent-labeled primers. When such a droplet passes through the droplet counter 312, the signal strength is higher than that of a droplet without the target DNA. A threshold 504 can be set to count the number of droplets having the target DNAs.

Figure 6:
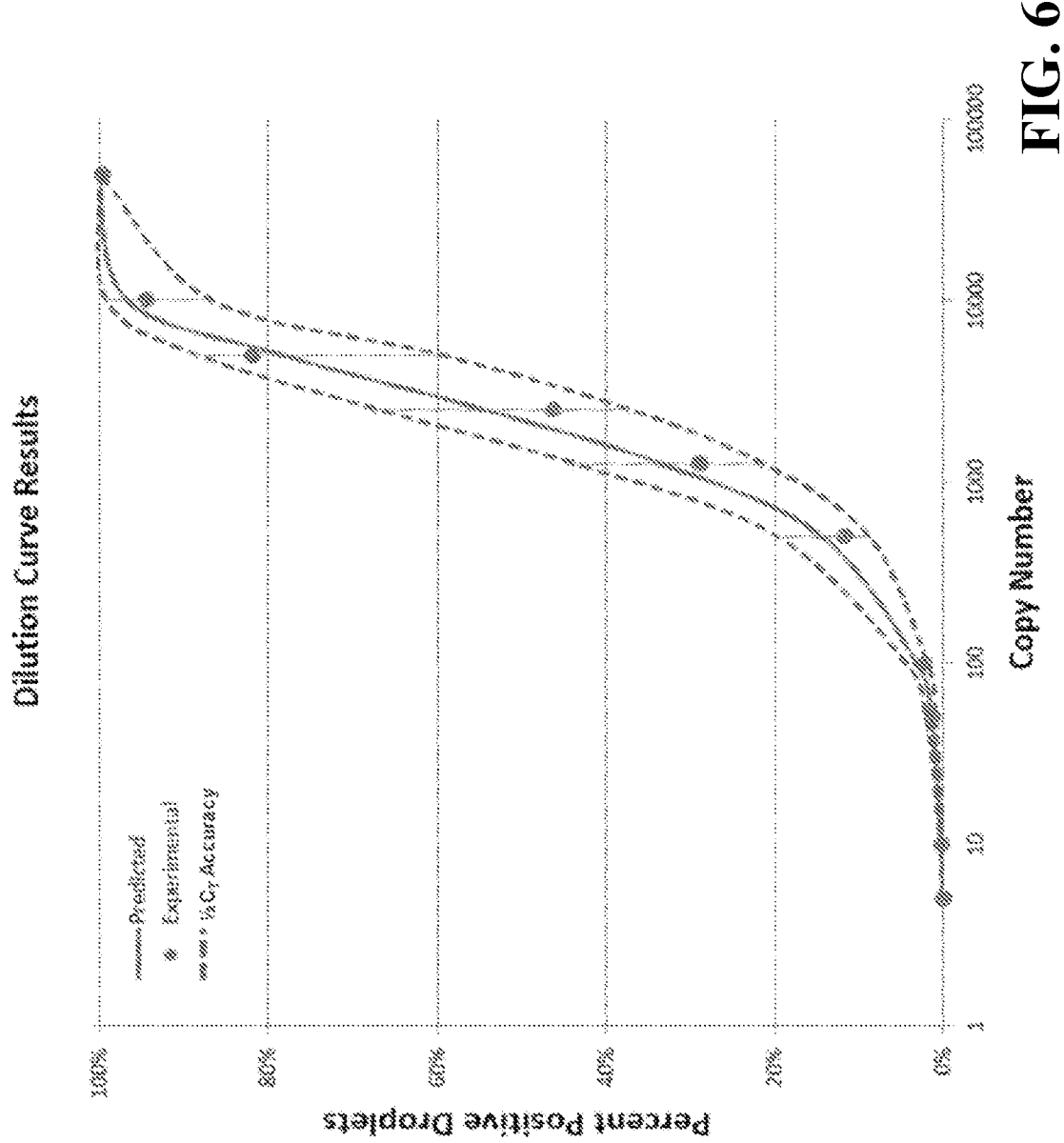
FIG. 6 is an example plot of percent positive droplets versus the number of copies of the DNA.

Referring to FIG. 6, the amount of a target sequence or gene that is present in the plurality of droplets measured by Applicants' apparatus is comparable to the amount of the target sequence or gene measured by real-time PCR, also called quantitative PCR (qPCR). A series of dilutions of the target sequence or gene is prepared and indicated by the series of copy numbers of the x-axis. $C_t$ (threshold cycle) is employed here to quantify the relative measure of the concentration of the target sequence or gene. The red dot indicates a measurement of the target sequence or gene at a different dilution of the sample measured by the current apparatus. FIG. 6 shows that the red dots are close to the predicted concentrations of the target sequence or gene at different dilutions of the sample and are well within the range of minus or plus 0.5 $C_t$ value of the concentrations of the target sequence or gene.

Figures 7A, 7B:
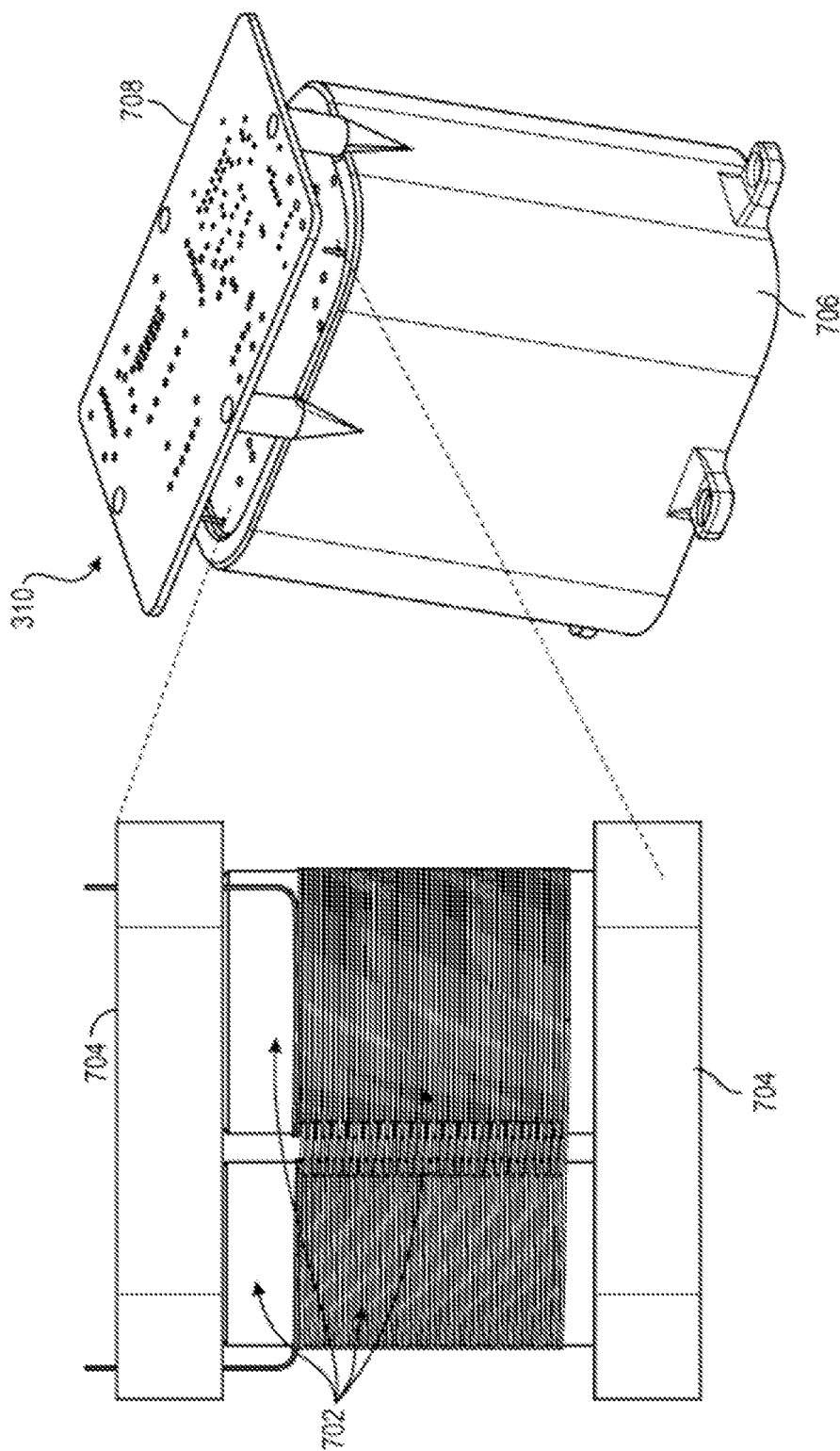
FIGS. 7(A)-(B) show schematics depicting an example thermocycler.

Specifically for real-time PCR, the thermocycler must have the ability to maintain a consistent temperature, as PCR amplification efficiency is dependent upon the temperature. Referring to FIGS. 7(A)-(B), schematics depicting an example thermocycler are provided. The thermocycler 310 comprises functioning components—heater cores 702 (in FIG. 7(A)). The heater cores 702 is covered with foam caps 704 to insulate and provide structural support for the heater cores 702. Together with the foam caps 704, the heater cores 702 are placed in a housing 706 that seals and insulates the cores 702. The temperature of the cores 702 are controlled by a circuit board 708 using the temperature as feedback.

Figure 8C:
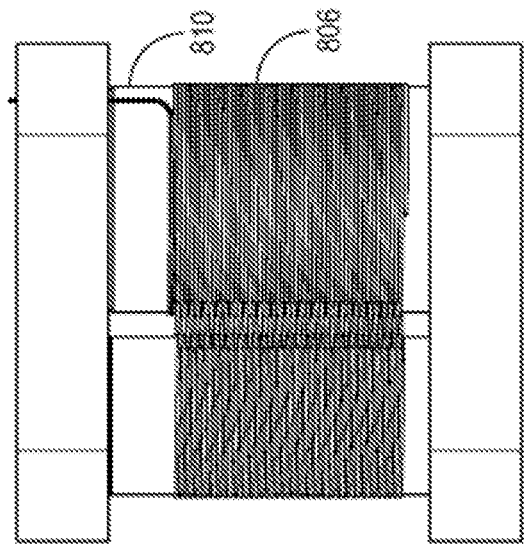
FIGS. 8(A)-(D) show schematics of the wraps of the heater cores in an example thermocycler.
Figure 8D:
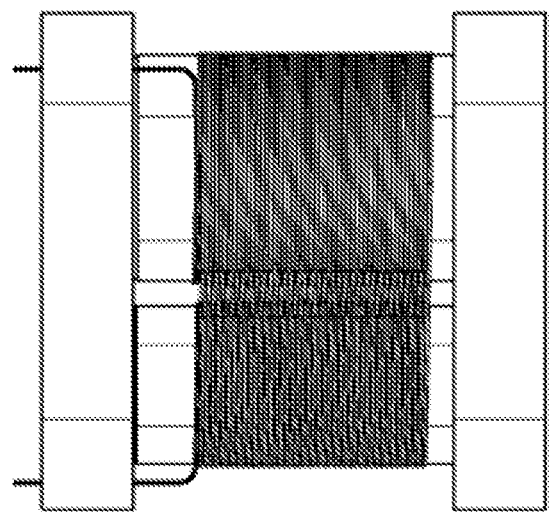
Figure 8A:
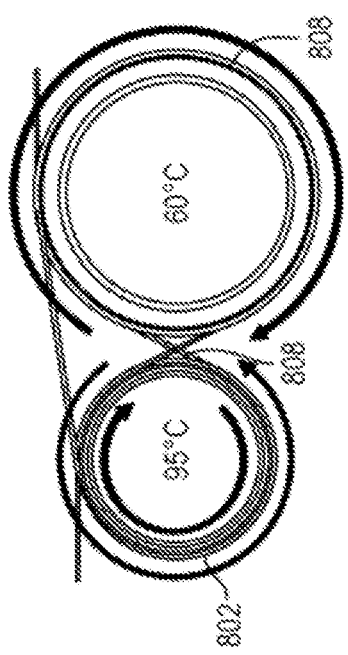
Figure 8B:
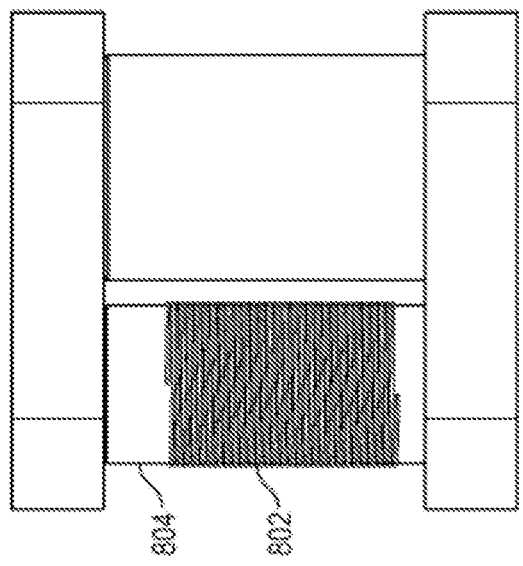
Figure 9:
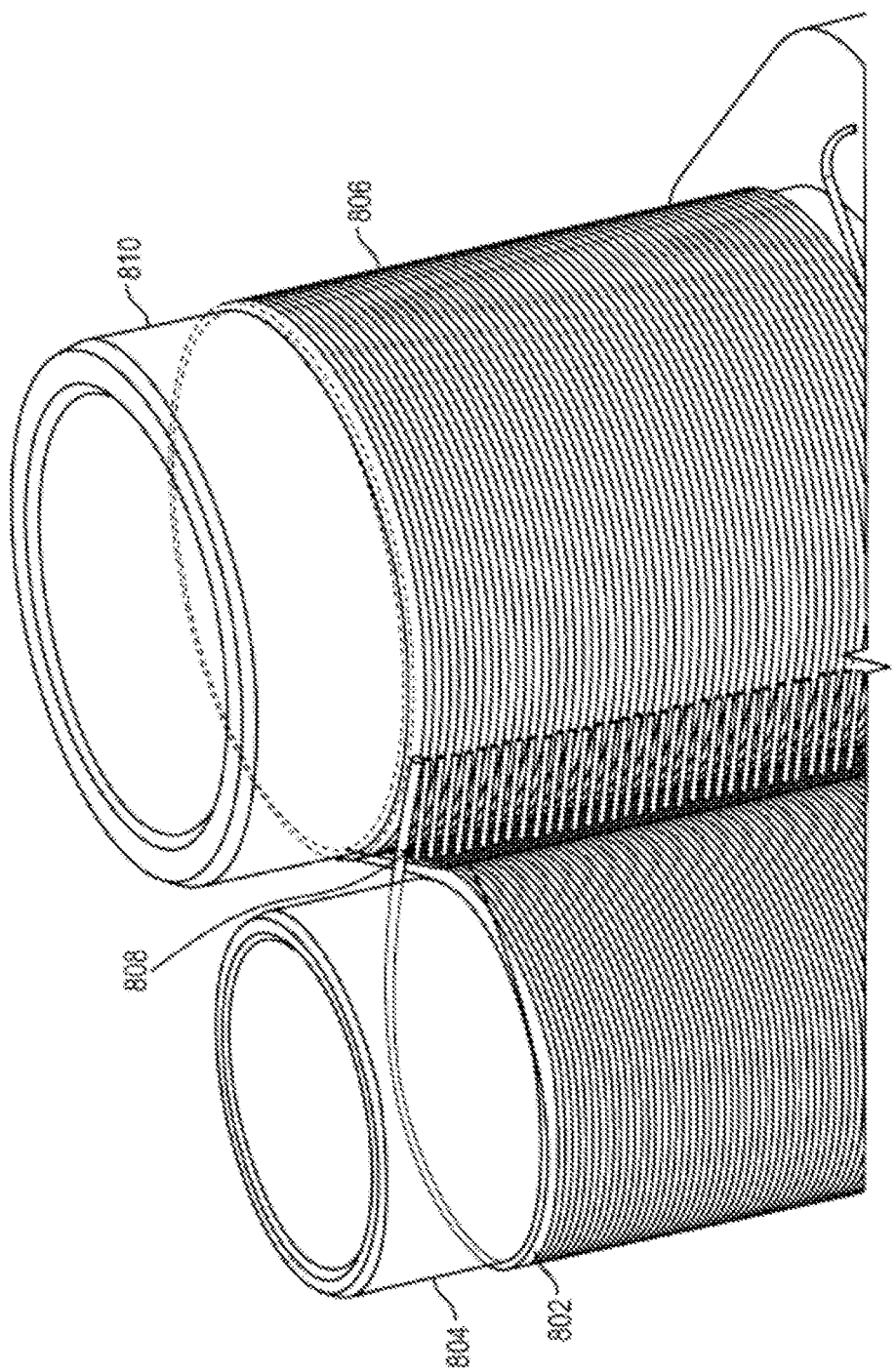
FIG. 9 shows an example interweaving mechanism of wraps in the heater cores of an example thermocycler.

Referring to FIGS. 8(A)-(D), schematics of the wiring of the heater cores of an example thermocycler are provided. The heater cores 702 comprises tubings and wraps around the tubings. The heater cores can comprise two tubings 804 and 810. For example, tubing 804 can be a 95° C. tubing having 40 continuous hot start wraps 802, and tubing 810 can a 60° C. tubing. Wraps for hot start are wrapped around one tubing 804 (in FIG. 8(B)) and thermocycle wraps 806 and 808 are wrapped around the other tubing 810 or both tubings (wraps 806 wrap around tubing 810 and wraps 808 wrap around both tubings 804 and 810, shown in FIG. 8(A)-(C)). As such, the hot start and thermocycle wraps are interweaved around tubing 804 as shown in FIGS. 8(A) and (D). The detail of an example interweaving mechanism is shown in FIG. 9. The thermocycle wraps 806 can flow downward. Two thermocycle wraps per cycle can be used to extend anneal time. Two wraps 808 of tubing 810 (e.g., a 60° C. tubing) can interweave with incoming wraps 802 around tubing 804 (e.g., a 95° C. tubing) to balance heat load distribution. When the two sets of wraps interweave, hot start wraps 802 flow in the opposite direction of thermocycle wraps 808 to balance heat load distribution (e.g., hot start wraps 802 flow upward with individual 95° C. thermocycle wraps 808 flowing downward). The wrap arrangement as disclosed herein can maintain more constant temperature at each point on the core, so the power consumption is lower for heating and cooling and, in turn, this more consistent temperature gives better results to the PCR reaction.

Figure 9A:
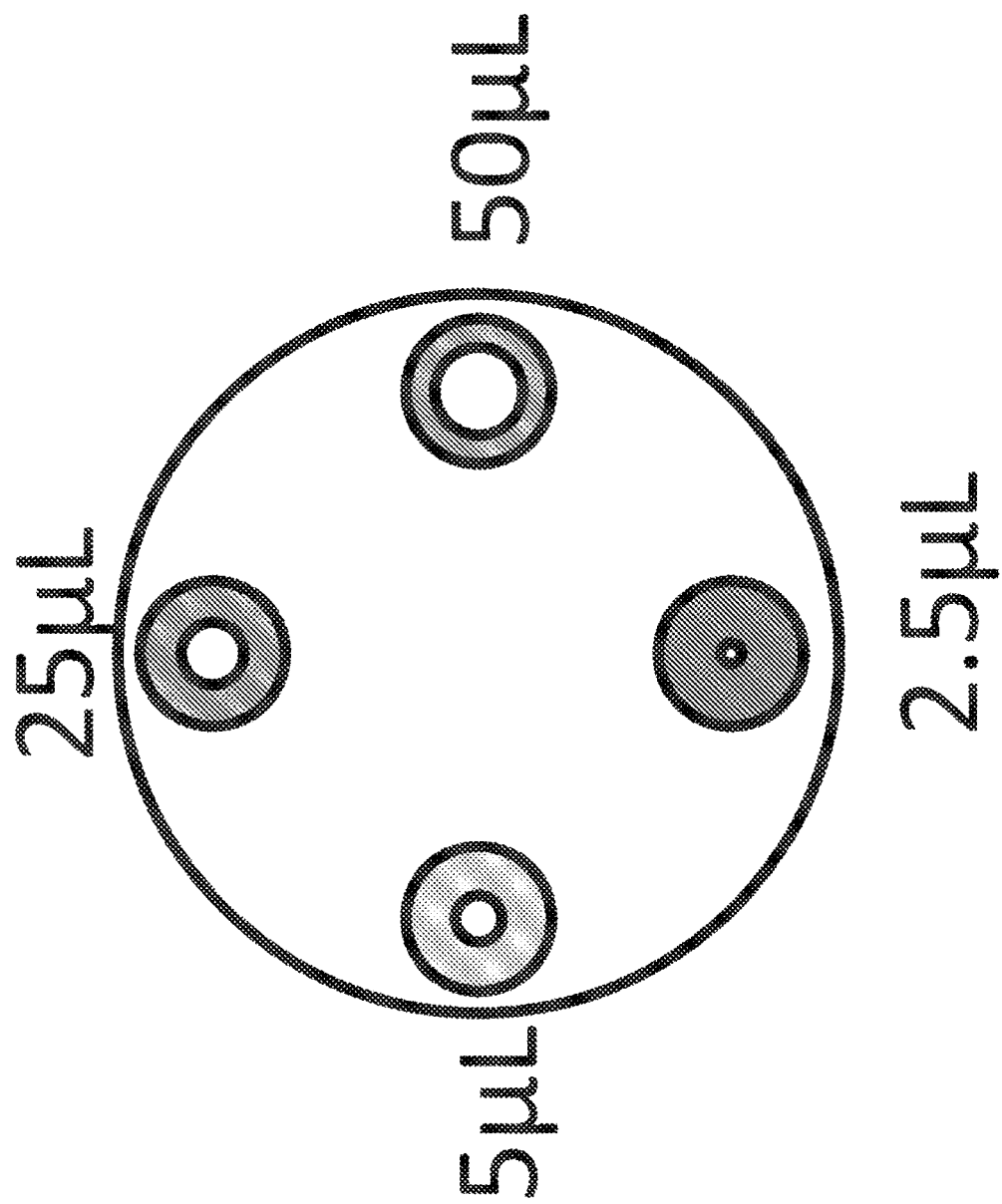
FIG. 9A shows a schematic diagram of the multiple inlet ports of an example injector.

The injector 302 can have multiple ports of different specific volumes (as shown in FIG. 9A, ports include sizes 2.5, 5, 25, and 50 microliters) and low dead volumes. The connections of the injectors can be Teflon or fluoroplastic. Such materials, like Teflon and fluoroplastic, have low surface energy and do not contaminate the sample. Because of the low surface energy, cleaning solutions do not absorb into the connections; thus, the injectors are bleach cleaning compatible and the connections can be reused.

Figure 10:
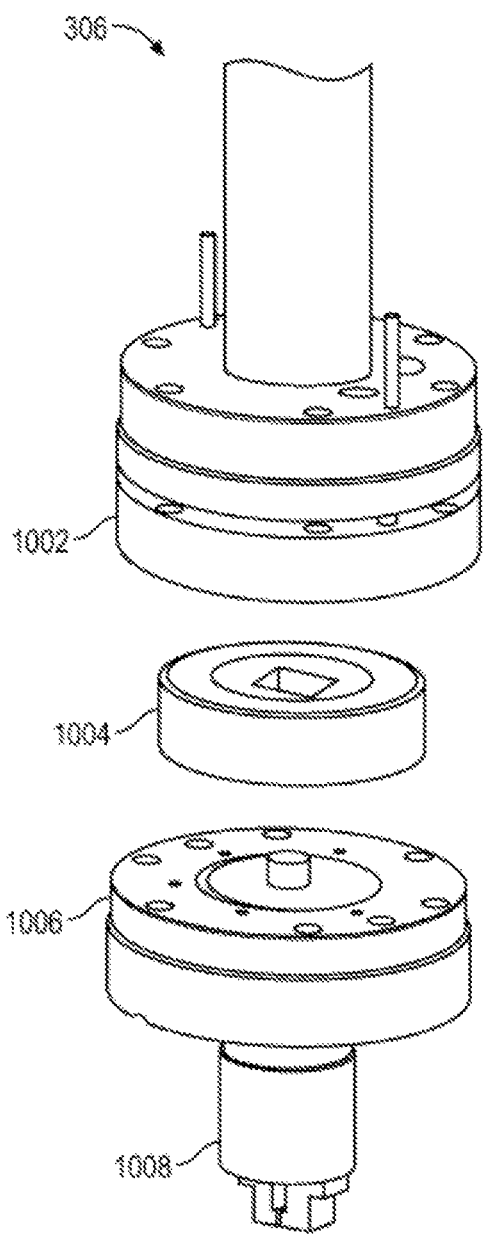
FIG. 10 show the structure of an example coalescing element.

Referring to FIG. 10, to combine all of the inserted reagents into a single reagent outlet a component may include outlet stator 1002, rotor with reagent chamber 1004, inlet stator 1006, and position encoder 1008. The stator can be made of Teflon. The reagent chamber can be initially filled with oil, such as fluorocarbon oil, to be used as carrier. The rotor 1004 may be rotated to fill reagent storage chamber with various reagents. Then high voltage field is used to induce electrocoalescence of all reagents. Afterwards, reagents and unneeded oil are flushed as waste through outlet to downstream processes. The fluid connections can be all Teflon or fluoroplastic. A vertical orientation with 60° cone angle may be used to allow for sample outlet at up to 45° tilt during operation. Arbitrary volumes may be be passed at arbitrary flow rates up to capacity of the chamber 1004. Buoyancy of reagents relative to fluid drives reagent close to packing. A rotor 1004 edge can automatically cleave inlet reagent to a specified volume. As the rotor 1004 turns, it cuts a cylindrical slug of reagent into smaller volumes of known volume.

The present invention has been described in terms of one or more preferred embodiments, and it should be appreciated that many equivalents, alternatives, variations, and modifications, aside from those expressly stated, are possible and within the scope of the invention. The appended document describes additional features of the present invention and is incorporated herein in its entirety by reference.

We claim:

1. A sample analyzing system, comprising:
   an injector that receives a sample, the injector comprising an injector inlet and an injector outlet;
   at least one mixer valve in fluid communication with the injector, the mixer receiving the sample from the injector and mixing the sample with a plurality of polymerase chain reaction (PCR) reagents to produce a reagent composition;
   a cassette in fluid communication with the at least one mixer and storing the plurality of PCR reagents including master mix, primers, probes, and diluent;
   a droplet generator receiving the reagent composition, the droplet generator comprising a generator inlet and a generator outlet for dispensing a plurality of droplets of the mixture;
   a thermocycler in fluid communication with the droplet generator and receiving the plurality of droplets of the mixture and performing PCR on the plurality of droplets;
   an optical detection apparatus in fluid communication with the thermocycler for quantifying at least one molecular target in droplets that contain the at least one molecular target;
   a controller comprising: a processor in signal communication with each of the injector, the mixer, the cassette, the droplet generator, the thermocycler, and the optical detection apparatus; and a non-transitory computer readable medium comprising program instructions executable by the processor to control the injector, the mixer, the cassette, the droplet generator, the thermocycler, and the optical detection apparatus; and
   a coalescer comprising: an inlet stator having a first plurality of apertures extending therethrough; an outlet stator having a second plurality of apertures extending therethrough; a rotor having a third plurality of apertures extending therethrough and an internal cavity, the rotor disposed between the inlet stator and the outlet stator, and a reagent chamber disposed within the internal cavity of the rotor, wherein the reagent chamber is configured to rotate along an edge of the rotor from one aperture to another, and wherein at least a portion of the reagent composition is produced by electrocoalescense within the reagent chamber.

2. The system of claim 1, wherein the reagent composition is produced by electrocoalescence of the sample with the plurality of PCR reagents.

3. The system of claim 1, wherein the sample comprises nucleic acids.

4. The system of claim 3, wherein the nucleic acids comprise DNAs.

5. The system of claim 1, wherein the reagent chamber comprises: a tubular container; a cone connecting to a first end of the container; and a receiver connecting to an apex of the cone and having a first side for receiving the plurality of PCR reagents and a second side for dispensing the reagent composition.

6. The system of claim 5, wherein the cone has a vertical angle sufficient to allow for sample outlet at up to 45° tilt during operation.

7. The system of claim 1, wherein the cassette comprises a housing and at least one chamber, wherein the chamber stores the plurality of PCR reagents.

8. The system of claim 1, wherein the droplet generator comprises a fluorophilic surface or a hydrophobic surface.

9. The system of claim 1, wherein the injector comprises a plurality of ports having different volumes.

10. The system of claim 1, wherein the injector comprises a fluorophilic surface or a hydrophobic surface.

11. The system of claim 1, wherein the thermocycler comprises a channel configured to direct the plurality of droplets, and wherein the channel is wrapped around at least two heater cores of the thermocycler.

12. The system of claim 1, wherein the thermocycler comprises:
   a plurality of heater cores; and
   a plurality of wires wrapped around the plurality of heater cores.

13. The system of claim 12, wherein the plurality of heater cores comprises a first heater core configured to maintain a first temperature and a second heater core configured to maintain a second temperature different than the first temperature.

14. The system of claim 12, wherein the plurality of wires comprises a first group of wires wrapped around the first heater core and a second group of wires wrapped around the second heater core.

15. The system of claim 14, wherein the second group of wires is wrapped around the first heater core and the second heater core.

16. The system of claim 14, wherein the first group of wires and the second group of wires are interwoven around the first heater core.

17. The system of claim 16, wherein the first group of wires is wrapped in the opposite direction of the second group of wires.

18. The system of claim 12, wherein the thermocycler further comprises a plurality of insulating blocks configured to support and insulate the plurality of heater cores.

19. The system of claim 1, wherein the optical detection apparatus is configured to detect a fluorescent signal.

* * * * *